United States Patent [19]
Hamilton et al.

[11] Patent Number: 5,935,989
[45] Date of Patent: Aug. 10, 1999

[54] N-LINKED UREAS AND CARBAMATES OF HETEROCYCLIC THIOESTERS

[75] Inventors: Gregory S. Hamilton, Catonsville; Jia-He Li, Cockeysville; Wei Huang, Baltimore, all of Md.

[73] Assignee: GPI NIL Holdings Inc., Wilmington, Del.

[21] Appl. No.: 08/775,585

[22] Filed: Dec. 31, 1996

[51] Int. Cl.$^6$ .......................... A61K 31/40; C07D 207/06
[52] U.S. Cl. ............................... 514/423; 548/533
[58] Field of Search .................... 548/543, 146, 548/311.1, 356.1, 492; 544/361; 546/183, 139, 286; 549/483, 1; 564/173; 514/423

[56] References Cited

U.S. PATENT DOCUMENTS

| | | | |
|---|---|---|---|
| 4,310,461 | 1/1982 | Krapcho et al. | 260/326 |
| 4,390,695 | 6/1983 | Krapcho et al. | 544/130 |
| 4,578,474 | 3/1986 | Krapcho et al. | 546/188 |
| 4,593,102 | 6/1986 | Shanklin | 546/216 |
| 4,596,819 | 6/1986 | Nicolaides et al. | 514/423 |
| 4,886,813 | 12/1989 | Nakamura et al. | 514/326 |
| 5,001,142 | 3/1991 | Trybulski et al. | 514/422 |
| 5,192,773 | 3/1993 | Armistead et al. | 514/315 |
| 5,276,207 | 1/1994 | Schneider et al. | 548/533 |
| 5,330,993 | 7/1994 | Armistead et al. | 514/330 |
| 5,385,918 | 1/1995 | Connell et al. | 514/330 |
| 5,541,191 | 7/1996 | Skotnicki et al. | 514/291 |
| 5,585,397 | 12/1996 | Tung et al. | 514/473 |

FOREIGN PATENT DOCUMENTS

| | | |
|---|---|---|
| WO 92/19593 | 11/1992 | WIPO . |
| WO 92/21313 | 12/1992 | WIPO . |
| WO 94/07858 | 4/1994 | WIPO . |
| WO 95/24385 | 9/1995 | WIPO . |
| WO 95/26337 | 10/1995 | WIPO . |
| WO 96/36630 | 11/1996 | WIPO . |
| WO 96/41609 | 12/1996 | WIPO . |

OTHER PUBLICATIONS

Yamishita, Dennis S. et al., "Design, Synthesis and Evolution of Dual Domain FKBP Ligands," Bioorg. Med. Chem. Lett., 1994, 4(2), 325–328.

Luengo, Juan I. et al., "Synthesis and Structure–Activity Relationships of Macrocyclic FKBP Ligands," Bioorg. Med. Chem. Lett., 1994 4(2), 321–324.

Holt, Dennis A. et al., "Structure–Activity Studies of Synthetic FKBP Ligands as Peptidyl–Prolyl Isomerase Inhibitors," Bioorg. Med. Chem. Lett., 1994, 4(2), 315–320.

Birkenshaw, Timothy N. et al., "Synthetic FKBP12 Ligands. Design and Synthesis of Pyranose Replacements," Bioorg. Med. Chem. Lett., 1994, 4(21), 2501–2506.

Holt, Dennis A. et al., "Design, Synthesis, and Kinetic Evaluation of High–Affinity FKBP Ligands and the X–ray Crystal Structure of Their Complexes with FKBP12," J. Am. Chem. Soc., 1993, 115, 9925–9938.

Wang, Gary T. et al., "Synthesis and FKBP Binding of Small Molecule Mimics of the Tricarbonyl Region of FK506," Biorg. Med. Chem. Lett., 1994, 4(9), 1161–1166.

Boulmedais, Ali et al., "Stereochimie de la reduction electrochimique d'a–cetoamides optiquement actives II. Electroreduction de benzoylflormamides derives de la S(-)–proline," Bull. Soc. Chim. Fr., 1988, 9(2), 185–191.

Dragovitch, Peter S. et al. "Structure–Based Design of Novel, Urea–Containing FKBP12 Inhibitors," J. Med. Chem., 1996, 39, 1872–1884.

Teague, Simon J. et al., "Synthesis and Study of a Non Macrocyclic FK506 Derivative," Bioorg. Med. Chem. Lett., 1994, 4(13), 1581–1584.

Dumont, Francis J. et al., "The Immunosuppressive and Toxic Effects of FK–506 are Mechanistically Related: Pharmacology of a Novel Antagonist of FK–506 and Rapamycin," J. Exp. Med., 1992, 176, 751–760.

Schreiber, Stuart L., "Chemistry and Biology of the Immunophilins and Their Immunosuppressive Ligands," Science, 1991, 251, 282–287.

*Primary Examiner*—Johann Richter
*Assistant Examiner*—Ebenezer Sackey
*Attorney, Agent, or Firm*—Gary M. Nath; Todd L. Juneau; Nath & Associates

[57] ABSTRACT

This invention relates to neurotrophic low molecular weight, small molecule N-linked ureas and carbamates of heterocyclic thioesters having an affinity for FKBP-type immunophilins, and their use as inhibitors of the enzyme activity associated with immunophilin proteins, particularly peptidyl-prolyl isomerase, or rotamase, enzyme activity.

21 Claims, No Drawings

5,935,989

N-LINKED UREAS AND CARBAMATES OF HETEROCYCLIC THIOESTERS

BACKGROUND OF THE INVENTION

1. Field of Invention

This invention relates to neurotrophic low molecular weight, small molecule N-linked ureas and carbamates of heterocyclic thioesters having an affinity for FKBP-type immunophilins, and their use as inhibitors of the enzyme activity associated with immunophilin proteins, particularly peptidyl-prolyl isomerase, or rotamase, enzyme activity.

2. Description of Related Art

The term immunophilin refers to a number of proteins that serve as receptors for the principal immunosuppressant drugs, cyclosporin A (CsA), FK506 and rapamycin. Known classes of immunophilins are cyclophilins and FK506 binding proteins, or FKBPs. Cyclosporin A binds to cyclophilin A while FK506 and rapamycin bind to FKBP12. These immunophilin-drug complexes interface with various intracellular signal transduction systems, especially the immune and nervous systems.

Immunophilins are known to have peptidyl-prolyl isomerase (PPIase), or rotamase, enzyme activity. It has been determined that rotamase enzyme activity plays a role in the catalyzation of the interconversion of the cis and trans isomers of peptide and protein substrates for the immunophilin proteins.

Immunophilins were originally discovered and studied in the immune tissue. It was initially postulated by those skilled in the art that inhibition of the immunophilins' rotamase activity leads to inhibition of T-cell proliferation, thereby causing the immunosuppressive activity exhibited by immunosuppressant drugs, such as cyclosporin A, FK506 and rapamycin. Further study has shown that the inhibition of rotamase activity, in and of itself, does not result in immunosuppressive activity. Schreiber et al., *Science*, 1990, vol. 250, pp. 556–559. Instead, immunosuppression appears to stem from the formulation of a complex of immunosuppressant drugs and immunophilins. It has been shown that the immunophilin-drug complexes interact with ternary protein targets as their mode of action. Schreiber et al., *Cell*, 1991, vol. 66, pp. 807–815. In the case of FKBP-FK506 and cyclophilin-CsA, the immunophilin-drug complexes bind to the enzyme calcineurin and inhibit the T-cell receptor signalling which leads to T-cell proliferation. Similarly, the immunophilin-drug complex of FKBP-rapamycin interacts with the RAFT1/FRAP protein and inhibits the IL-2 receptor signalling.

Immunophilins have been found to be present at high concentrations in the central nervous system. Immunophilins are enriched 10–50 times more in the central nervous system than in the immune system. Within neural tissues, immunophilins appear to influence nitric oxide synthesis, neurotransmitter release and neuronal process extension.

It has been found that picomolar concentrations of an immunosuppressant such as FK506 and rapamycin stimulate neurite outgrowth in PC12 cells and sensory neurons, namely dorsal root ganglion cells (DRGs). Lyons et al., *Proc. of Natl. Acad. Sci.*, 1994, vol. 91, pp. 3191–3195. In whole animal experiments, FK506 has been shown to stimulate nerve regeneration following facial nerve injury.

Surprisingly, it has been found that certain compounds with a high affinity for FKBPs are potent rotamase inhibitors and exhibit excellent neurotrophic effects. Furthermore, these rotamase inhibitors are devoid of immunosuppressive activity. These findings suggest the use of rotamase inhibitors in treating various peripheral neuropathies and enhancing neuronal regrowth in the central nervous system (CNS). Studies have demonstrated that neurodegenerative disorders such as Alzheimer's disease, Parkinson's disease, and amyotrophic lateral sclerosis (ALS) may occur due to the loss, or decreased availability, of a neurotrophic substance specific for a particular population of neurons affected in the disorder.

Several neurotrophic factors affecting specific neuronal populations in the central nervous system have been identified. For example, it has been hypothesized that Alzheimer's disease results from a decrease or loss of nerve growth factor (NGF). It has thus been proposed to treat Senile Dementia of the Alzheimer's Type (SDAT) patients with exogenous nerve growth factor or other neurotrophic proteins, such as brain derived growth factor, glial derived growth factor, ciliary neurotrophic factor and neurotropin-3, to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressant drugs exhibit a number of potentially serious side effects including nephrotoxicity, such as impairment of glomerular filtration and irreversible interstitial fibrosis (Kopp et al., *J. Am. Soc. Nephrol.*, 1991, 1:162); neurological deficits, such as involuntary tremors, or non-specific cerebral angina, such as non-localized headaches (De Groen et al., *N. Engl. J. Med.*, 1987, 317:861); and vascular hypertension with complications resulting therefrom (Kahan et al., *N. Engl. J. Med.*, 1989, 321:1725).

In order to prevent the side effects associated with use of the immunosuppressant compounds, the present invention provides non-immunosuppressive compounds containing small molecule FKBP rotamase inhibitors for enhancing neurite outgrowth, and promoting neuronal growth and regeneration in various neuropathological situations where neuronal repair can be facilitated, including: peripheral nerve damage caused by physical injury or disease state such as diabetes; physical damage to the central nervous system (spinal cord and brain); brain damage associated with stroke; and neurological disorders relating to neurodegeneration, such as Parkinson's disease, SDAT (Alzheimer's disease), and amyotrophic lateral sclerosis.

SUMMARY OF THE INVENTION

The present invention relates to neurozrophic low molecular weight, small molecule compounds having an affinity for FKBP-type immunophilins. Once bound to these proteins, the neurotrophic compounds are potent inhibitors of the enzyme activity associated with immunophilin proteins, particularly peptidyl-prolyl isomerase, or rotamase, enzyme activity. A key feature of the compounds of the present invention is that they do not exert any significant immunosuppressive activity in addition to their neurotrophic activity. Another significant feature is the novel addition of a thioester linkage and an unexpected increase in bioavailability and potency as compared to compounds lacking a thioester linkage.

Specifically, the present invention relates to a compound of formula I:

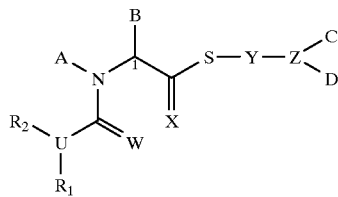

I or a pharmaceutically acceptable salt thereof, wherein:

A and B are taken together, with the nitrogen and carbon atoms to which they are respectively attached, to form a 5–7 membered saturated or unsaturated heterocyclic ring containing any combination of $CH_2$, O, S, SO, $SO_2$, NH or $NR_3$ in any chemically stable oxidation state;

X is either O or S;

Y is a direct bond to Z, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

Z is a direct bond, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

C and D are independently:

hydrogen, or Ar, or $C_1$–$C_6$ straight or branched chain alkyl or alkenyl which is optionally substituted in one or more position(s) with $C_3$–$C_8$ cycloalkyl, $C_5$–$C_7$ cycloalkenyl, hydroxyl, carbonyl oxygen, or with Ar, where said alkyl, alkenyl, cycloalkyl or cycloalkenyl groups is optionally substituted with $C_1$–$C_4$ alkyl, $C_1$–$C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

wherein Ar is a mono-, bi- or tricyclic, carbo- or heterocyclic ring, wherein the rings are either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, or a combination thereof; wherein aromatic or tertiary alkyl amines are optionally oxidized to a corresponding N-oxide;

W is oxygen or sulfur;

U is either O or N, wherein when U is O, then $R_1$ is a lone pair of electrons and $R_2$ is selected from the group consisting of Ar, as defined above, or C3–C8 cycloalkyl, or $C_1$–$C_6$ straight or branched chain alkyl or alkenyl, or $C_1$–$C_6$ straight or branched chain alkyl or alkenyl substituted in one or more positions with Ar as defined above, or with C3–C8 cycloalkyl;

and when U is N, $R_1$ and $R_2$ are selected independently from the group consisting of Hydrogen, or Ar, as defined above, or C3–C8 cycloalkyl, or $C_1$–$C_6$ straight or branched chain alkyl or alkenyl, or $C_1$–$C_6$ straight or branched chain alkyl or alkenyl substituted in one or more positions with Ar as defined above, or with C3–C8 cycloalkyl, or R1 and R2 may be taken together to form a heterocyclic 5 or 6 membered ring selected from the following: pyrrolidine, imidazolidine, pyrazolidine, piperidine, and piperazine.

In preferred embodiments, Ar is selected from the group consisting of naphthyl, indolyl, furyl, thiazolyl, thienyl, pyridyl, and phenyl.

A preferred embodiment of this invention is a compound of formula II:

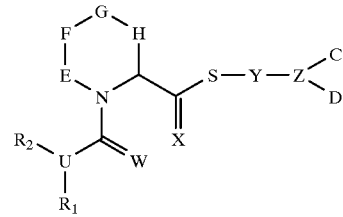

II or a pharmaceutically acceptable salt thereof, wherein:

E, F, G and H are independently $CH_2$, O, S, SO, $SO_2$, NH or $NR_3$;

X is either O or S;

Y is a direct bond to Z, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

Z is a direct bond, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

C and D are independently:

hydrogen, or Ar, or $C_1$–$C_6$ straight or branched chain alkyl or alkenyl, which is optionally substituted in one or more position(s) with $C_3$–$C_8$ cycloalkyl, $C_5$–$C_7$ cycloalkenyl, hydroxyl, carbonyl oxygen, or with Ar, where said alkyl, alkenyl, cycloalkyl or cycloalkenyl groups is optionally substituted with $C_1$–$C_4$ alkyl, $C_1$–$C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

wherein Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof; wherein aromatic or tertiary alkyl amines are optionally oxidized to a corresponding N-oxide;

W is oxygen or sulfur;

U is either O or N, wherein when U is O, then $R_1$ is a lone pair of electrons and $R_2$ is selected from the group consisting of Ar, as defined above, or C3–C8 cycloalkyl, or $C_1$–$C_6$ straight or branched chain alkyl or alkenyl, or $C_1$–$C_6$ straight or branched chain alkyl or alkenyl substituted in one or more positions with Ar as defined above, or with C3–C8 cycloalkyl;

and when U is N, $R_1$ and $R_2$ are selected independently from the group consisting of Hydrogen, or Ar, as defined above, or C3–C8 cycloalkyl, or $C_1$–$C_6$ straight or branched chain alkyl or alkenyl, or $C_1$–$C_6$ straight or branched chain alkyl or alkenyl substituted in one or more positions with Ar as defined above, or with C3–C8 cycloalkyl, or R1 and R2 may be taken together to form a heterocyclic 5 or 6 membered ring selected from the following: pyrrolidine, imidazolidine, pyrazolidine, piperidine, and piperazine.

In preferred embodiments, Ar is selected from the group consisting of naphthyl, indolyl, furyl, thiazolyl, thienyl, pyridyl, and phenyl.

Another preferred embodiment is a compound of formula III:

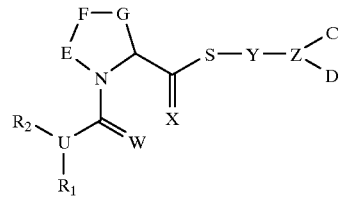

or a pharmaceutically acceptable salt thereof, wherein:

E, F, and G are independently $CH_2$, O, S, SO, $SO_2$, NH or $NR_3$;

X is either O or S;

Y is a direct bond to Z, or a $C_1$–$C_6$ straight or branched chain alkyl or alkenyl, wherein any of the carbon atoms of said alkyl or alkenyl is optionally substituted in one or more positions with oxygen to form a carbonyl, of wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

Z is a direct bond, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

C and D are independently:

hydrogen, or Ar, or $C_3$–$C_6$ straight or branched chain alkyl or alkenyl, which is optionally substituted in one or more position(s) with $C_3$–$C_8$ cycloalkyl, $C_5$–$C_7$ cycloalkenyl, hydroxyl, carbonyl oxygen, or with Ar, where said alkyl, alkenyl, cycloalkyl or cycloalkenyl groups is optionally substituted with $C_1$–$C_4$ alkyl, $C_1$–$C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

wherein Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof; wherein aromatic or tertiary alkyl amines are optionally oxidized to a corresponding N-oxide;

W is oxygen or sulfur;

U is either O or N, wherein when U is O, then $R_1$ is a lone pair of electrons and $R_2$ is selected from the group consisting of
Ar, as defined above, or
C3–C8 cycloalkyl, or
$C_1$–$C_6$ straight or branched chain alkyl or alkenyl, or
$C_1$–$C_6$ straight or branched chain alkyl or alkenyl substituted in one or more positions with Ar as defined above, or with C3–C8 cycloalkyl;

and when U is N, $R_1$ and $R_2$ are selected independently from the group consisting of
Hydrogen, or
Ar, as defined above, or
C3–C8 cycloalkyl, or
$C_1$–$C_6$ straight or branched chain alkyl or alkenyl, or
$C_1$–$C_6$ straight or branched chain alkyl or alkenyl substituted in one or more positions with Ar as defined above, or with C3–C8 cycloalkyl,
or R1 and R2 may be taken together to form a heterocyclic 5 or 6 membered ring selected from the following: pyrrolidine, imidazolidine, pyrazolidine, piperidine, and piperazine.

In preferred embodiments, Ar is selected from the group consisting of naphthyl, indolyl, furyl, thiazolyl, thienyl, pyridyl, and phenyl.

A further particularly preferred embodiment of this invention is a compound of formula IV:

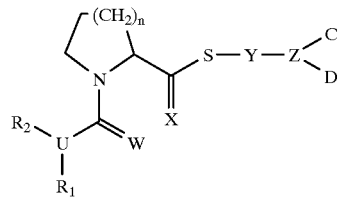

IV or a pharmaceutically acceptable salt thereof, wherein:
n is 1, 2 or 3 forming a 5–7 member heterocyclic ring;
X is either O or S;
Y is a direct bond to Z, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

Z is a direct bond, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

C and D are independently:

hydrogen, or Ar, or $C_1$–$C_6$ straight or branched chain alkyl or alkenyl, which is optionally substituted in one or more positions with $C_3$–$C_8$ cycloalkyl, $C_5$–$C_7$ cycloalkenyl, hydroxyl, carbonyl oxygen, or with Ar, where said alkyl, alkenyl, cycloalkyl or cycloalkenyl groups is optionally substituted with $C_1$–$C_4$ alkyl, $C_1$–$C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

wherein Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof; wherein aromatic or tertiary alkyl amines are optionally oxidized to a corresponding N-oxide;

W is oxygen or sulfur;

U is either O or N, wherein when U is O, then $R_1$ is a lone pair of electrons and $R_2$ is selected from the group consisting of Ar, as defined above, or C3–C8 cycloalkyl, or $C_1$–$C_6$ straight or branched chain alkyl or alkenyl, or $C_1$–$C_6$ straight or branched chain alkyl or alkenyl substituted in one or more positions with Ar as defined above, or with C3–C8 cycloalkyl;

and when U is N, $R_1$ and $R_2$ are selected independently from the group consisting of Hydrogen, or Ar, as defined above, or C3–C8 cycloalkyl, or $C_1$–$C_6$ straight or branched chain alkyl or alkenyl, or $C_1$–$C_6$ straight or branched chain alkyl or alkenyl substituted in one or more positions with Ar as defined above, or with C3–C8 cycloalkyl, or R1 and R2 may be taken together to form a heterocyclic 5 or 6 membered ring selected from the following: pyrrolidine, imidazolidine, pyrazolidine, piperidine, and piperazine.

In preferred embodiments, Ar is selected from the group consisting of naphthyl, indolyl, furyl, thiazolyl, thienyl, pyridyl, and phenyl.

Particularly preferred compounds of the present invention are selected from the group consisting of:

3-(3-Pyridyl)-1-propyl-2S-1-[(2-methylbutyl) carbamoyl] pyrrolidine-2-carboxylate;

3-(3-Pyridyl)-1-propyl-2S-1-[(1',1'-Dimethylpropyl) carbamoyl]pyrrolidine-2-carboxylate; and 3-(3-Pyridyl)-1-propyl-2S-1-[(cyclohexyl) thiocarbamoyl] pyrrolidine-2-carboxylate.

The present invention also relates to a pharmaceutical composition comprising a neurotrophically effective amount of the compound of formula I, II, III or IV, and a pharmaceutically acceptable carrier.

The present invention further relates to a method of effecting a neuronal activity in an animal, comprising:

administering to the animal a neurotrophically effective amount of the compound of formula I, II, III or IV.

DETAILED DESCRIPTION OF THE INVENTION

Definitions

"Alkyl" means a branched or unbranched saturated hydrocarbon chain containing 1 to 6 carbon atoms, such as methyl, ethyl, propyl, iso-propyl, butyl, iso-butyl, tert-butyl, n-pentyl, n-hexyl, and the like, unless otherwise indicated.

"Alkoxy" means the group —OR wherein R is alkyl as herein defined. Preferably, R is a branched or unbranched saturated hydrocarbon chain containing 1 to 3 carbon atoms.

"Halo" means fluoro, chloro, bromo, or iodo, unless otherwise indicated.

"Phenyl" includes all possible isomeric phenyl radicals, optionally monosubstituted or multi-substituted with substituents selected from the group consisting of alkyl, alkoxy, hydroxy, halo, and haloalkyl.

The term "pharmaceutically acceptable salt" refers to salts of the subject compounds which posses the desired pharmacological activity and which are neither biologically nor otherwise undesirable. The salts can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds of this invention possess at least one asymmetric center and thus can be produced as mixtures of stereoisomers or as individual stereoisomers. The individual diastereomers or enantiomers may be obtained by using an optically active starting material, by resolving a racemic or non-racemic mixture of an intermediate at some appropriate stage of the synthesis, or by resolution of the compound of formula (I). It is understood that the individual diastereomers or enantiomers as well as mixtures (racemic and non-racemic) of diastereomers or enantiomers are encompassed by the scope of the present invention. The S-steroisomer at atom 1 of formula I is most preferred due to its greater activity.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror images of each other.

"Racemic mixture" means a mixture containing equal parts of individual enantiomers. "Non-racemic mixture" is a mixture containing unequal parts of individual enantiomers or stereoisomers.

The term "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

The system used in naming the compounds of the present invention is shown below, using a compound of formula IV as an example.

A compound of the present invention, especially Formula IV, wherein n is 1, X is O, Y is $(CH_2)_2$, Z is CH, C is 3-pyridyl, D is H, W is O, U is N, R1 is H and R2 is 2-methylbutyl, is named 3-(3-pyridyl)-1-propylmercaptyl (2s)-1-[(2-methylbutyl) carbamoyl] pyrrolidine-2-carboxylate.

Compounds of the Invention

The neurotrophic low molecular weight, small molecule FKBP inhibitor compounds of this invention have an affinity for FKBP-type immunophilins, such as FKBP12. When the neurotrophic compounds of this invention are bound to an FKBP-type immunophilin, they have been found to inhibit the prolyl-peptidyl cis-trans isomerase activity, or rotamase, activity of the binding protein and unexpectedly stimulate neurite growth.

Specific exemplifications of these embodiments are presented in TABLE I.

3-(3-Pyridyl)-1-propyl-2S-1-[(1', 1'-Dimethylpropyl) carbamoyl]pyrrolidine-2-carboxylate; and
3-(3-Pyridyl)-1-propyl-2S-1-[(cyclohexyl) thiocarbamoyl] pyrrolidine-2-carboxylate.

The compounds of the present invention exist as stereoisomeric forms, either enantiomers or diastereoisomers. Included within the scope of the invention are the enantiomers, the racemic form, and diastereoisomeric mixtures. Enantiomers and diastereoisomers can be separated by methods known to those skilled in the art.

Methods of Using the Compounds of the Invention

The compounds of the present invention have an affinity for the FK506 binding protein, particularly FKBP12, which is present in the neuronal tissue. When the inventive compounds bind to FKBP in neuronal tissue, they exhibit excellent neurotrophic activity. This activity is useful in the stimulation of damaged neurons, the promotion of neuronal regeneration, the prevention of neurodegeneration, and the treatment of several neurological disorders known to be associated with neuronal degeneration and peripheral neuropathies.

For the foregoing reasons, the present invention further relates to a method of effecting a neuronal activity in an animal, comprising:

administering to the animal a neurotrophically effective amount of a compound of formula I, II, III or IV.

TABLE I

COMPOUNDS

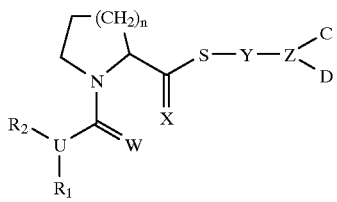

| No. | n | W | Y | Z | C | D | R1 | R2 |
|---|---|---|---|---|---|---|---|---|
| 1 | 1 | O | $(CH_2)_2$ | CH | 3-Pyridyl | H | H | 2-Methylbutyl |
| 2 | 1 | O | $(CH_2)_2$ | CH | 3-Pyridyl | H | H | 1,1-dimethylpropyl |
| 3 | 1 | O | $(CH_2)_2$ | CH | 4-Methoxy phenyl | H | H | 1,1-dimethylpropyl |
| 4 | 1 | O | $CH_2$ | CH | Phenyl | H | H | 1,1-dimethylpropyl |
| 5 | 1 | S | $(CH_2)_2$ | CH | 4-Methoxy phenyl | H | H | Cyclohexyl |
| 6 | 1 | O | $(CH_2)_2$ | CH | 3-Pyridyl | H | H | Cyclohexyl |
| 7 | 1 | S | $(CH_2)_2$ | CH | 3-Pyridyl | H | H | Cyclohexyl |
| 8 | 1 | S | $(CH_2)_2$ | CH | 3-Pyridyl | H | H | 1-Adamantyl |
| 9 | 1 | S | $(CH_2)_2$ | CH | 3-Pyridyl | H | H | 1,1-dimethylpropyl |
| 10 | 1 | O | $(CH_2)_2$ | CH | Phenyl | Phenyl | H | 1,1-dimethylpropyl |
| 11 | 2 | O | $(CH_2)_2$ | CH | Phenyl | H | H | 1,1-dimethylpropyl |
| 12 | 2 | O | $(CH_2)_2$ | CH | Phenyl | H | H | Phenyl |
| 13 | 2 | O | Direct Bond | CH | 2-Phenyl ethyl | 2-Phenyl ethyl | H | Phenyl |
| 14 | 2 | O | Direct Bond | CH | 2-Phenyl ethyl | 2-Phenyl ethyl | H | Cyclohexyl |
| 15 | 2 | S | Direct Bond | CH | 2-Phenyl ethyl | 2-Phenyl ethyl | H | Cyclohexyl |
| 16 | 2 | O | $(CH_2)_2$ | CH | 4-Methoxy phenyl | H | H | Cyclohexyl |

The most preferred compounds of formula IV are:
3-(3-Pyridyl)-1-propyl-2S-1-[(2-methylbutyl) carbamoyl] pyrrolidine-2-carboxylate;

In a preferred embodiment, the neuronal activity is selected from the group consisting of stimulation of damaged neurons, promotion of neuronal regeneration, prevention of neurodegeneration and treatment of neurological disorder.

The neurological disorders that may be treated include but are not limited to: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated; ruptured or prolapsed invertabrae disk syndromes; cervical spondylosis; plexus disorders; thoracic outlet destruction syndromes; peripheral neuropathic such as those caused by lead, dapsone, ticks, porphyria, or Guillain-Barré syndrome; Alzheimer's disease; and Parkinson's disease.

The compounds of the present invention are particularly useful for treating a neurological disorder selected from the group consisting of: peripheral neuropathy caused by physical injury or disease state, physical damage to the brain, physical damage to the spinal cord, stroke associated with brain damage, and neurological disorder relating to neurodegeneration. Examples of neurological disorders relating to neurodegeneration are Alzheimer's Disease, Parkinson's Disease, and amyotrophic lateral sclerosis.

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for adminstration to the brain.

The compounds of the present invention may be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil may be employed including synthetic mono- or di-glycerides. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

The compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds of this invention may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

The compounds of this invention may also be administered topically, especially when the conditions addressed for treatment involve areas or organs readily accessible by topical application, including neurological disorders of the eye, the skin, or the lower intestinal tract. Suitable topical formulations are readily prepared for each of these areas.

For topical application to the eye, or ophthalmic use, the compounds can be formulated as micronized suspensions in isotonic, pH adjusted sterile saline, or, preferably, as solutions in isotonic, pH adjusted sterile saline, either with or without a preservative such as benzylalkonium chloride. Alternatively for the ophthalmic uses the compounds may be formulated in an ointment such as petrolatum.

For topical application to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see above) or in a suitable enema formulation.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

Pharmaceutical Compositions of the Invention

The present invention also relates to a pharmaceutical composition comprising:

(i) a neurotrophically effective amount of the compound of formula I, II, III or IV, and (ii) a pharmaceutically acceptable carrier.

The above discussion relating to the utility and administration of the compounds of the present invention also applies to the pharmaceutical compositions of the present invention.

Methods of Making the Compounds of the Invention

The novel compounds of this invention may be readily prepared by standard techniques of organic chemistry, utilizing the general synthetic pathway depicted below. As described by Scheme I, cyclic amino acids 1 protected by suitable blocking groups P on the amino acid nitrogen may be reacted with thiols RSH to generate thioesters 2. After removal of the protecting group, the free amine 3 may be reacted with a variety of isocyanates or isothiocyanates to provide the final ureas or thioureas, respectively.

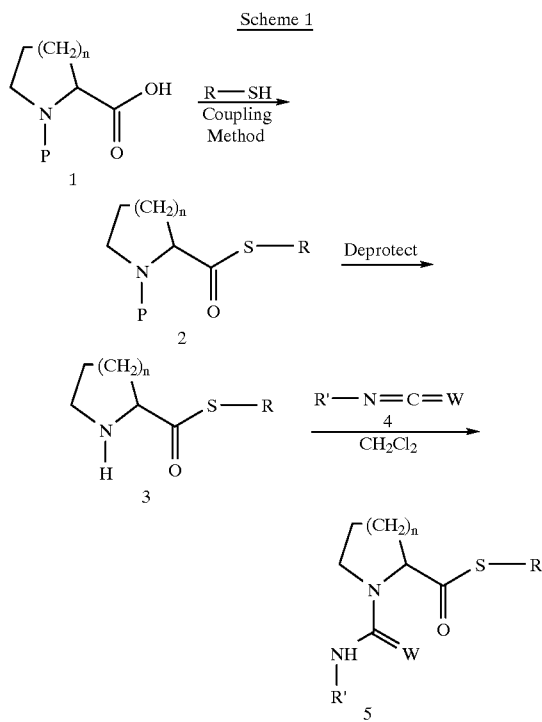

Isocyanates (R'NCO) or isothiocyanates (R'NCS) 4 may be conveniently prepared from the corresponding readily available amines by reaction with phosgene or thiophosgene, as depicted in Scheme II.

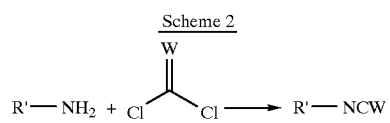

Thiols R—SH may be conveniently prepared from the corresponding readily available alcohols or halides via a two step replacement of halide by sulfur, as described in Scheme III. Halides may be reacted with thiourea, and the corresponding alkyl thiouronium salts hydrolyzed to provide thiols RSH. If alcohols are used as the starting materials, they may be first converted to the corresponding halides by standard methods.

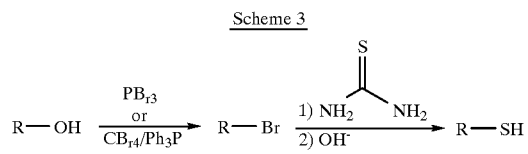

EXAMPLES

The following examples are illustrative of the present invention and are not intended to be limitations thereon. Unless otherwise specified, all percentages are based on 100% by weight of the final compound.

Example 1

Synthesis of 3-(3-Pyridyl)-1-propylmercaptyl 2S-1-[(2-methylbutyl)carbamoyl]pyrrolidine-2-carboxylate (1)

3-(3-Pyridyl)-1-propylchloride

To a solution of 3-(3-pyridyl)-1-propanol (10 g; 72.4 mmol) in chloroform (100 mL) was added dropwise a solution of thionyl chloride (12.9 g; 108.6 mmol) in chloroform (50 mL). The resulting mixture was refluxed for 1 hour, then poured into ice-cold 50% aqueous potassium hydroxide (150 mL). The layers were separated, and the organic phase was dried, concentrated, and purified on a silica gel column, eluting with 40% ethylacetate in hexane, to obtain 10 g (65%) of the chloride as a clear oil, $^1$H NMR (300 MHz, CDCl$_3$): δ2.02–2.11 (m, 2H); 2.77 (m, 2H); 3.51 (m, 2H); 7.20 (m, 1H); 7.49 (m, 1H); 8.45 (m, 2H).

3-(3-Pyridyl)-1-propylmercaptan

A mixture of 3-(3-pyridyl)-1-propylchloride (3 g; 19.4 mmol) and thiourea (1.48 g; 19.4 mmol) in ethanol (10 mL) was refluxed for 24 hours. Aqueous sodium hydroxide, 15 mL of a 0.75N solution, was added, and the mixture was refluxed for an additional 2 hrs. After cooling to room temperature, the solvent was removed in vacuo. Chromatographic purification of the crude thiol on a silica gel column eluting with 50% ethyl acetate in hexane delivered 1.2 g of 3-(3-Pyridyl)-1-propylmercaptan as a clear liquid $^1$H NMR (300 MHz, CDCl$_3$): δ1.34 (m, 1H); 1.90 (m, 2H); 2.52 (m, 2H); 2.71 (m, 2H); 7.81 (m, 1H); 7.47 (m, 1H); 8.42 (m, 2H).

3-(3-Pyridyl)-1-propylmercaptyl N-(tert-butyloxycarbonyl)pyrrolidine-2-carboxylate A mixture of N-(tert-butylyoxycarbonyl)-(S)-proline (3.0 g; 13.9 mmol); 3-(3-Pyridyl)-1-propylmercaptan (3.20 g; 20.9 mmol), dicyclohexylcarbodiimide (4.59 g; 22.24 mmol), camphorsulfonic acid (1.08 g; 4.63 mmol), and 4-dimethylaminopyridine (0.60 g; 4.63 mmol) in dry methylene chloride (100 mL) was stirred overnight. The reaction mixture was diluted with methylene chloride (50 mL) and water (100 mL), and the layers were separated. The organic phase was washed with water (3×100 mL), dried over magnesium sulfate, and concentrated, and the crude residue was purified on a silica gel column eluting with ethyl acetate to obtain 4.60 g (95%) of the thioester as a thick oil, $^1$H NMR (300 MHz, CDCl$_3$): δ1.45 (s, 9H) ; 1.70–2.05 (m, 5H); 2.32 (m, 1H); 2.71 (t, 2H); 2.85 (m, 2H); 3.50 (m, 2H); 4.18 (m, 1H); 7.24 (m, 1H); 7.51 (m, 1H) ; 8.48 (m, 2H).

3-(3-Pyridyl)-1-propylmercaptyl pyrrolidine-2-carboxylate

A solution of 3-(3-Pyridyl)-1-mercaptyl N-(tert-butylyoxycarbonyl)pyrrolidine-2-carboxylate (4.60 g; 13.1 mmol) in methylene chloride (60 mL) and trifluoroacetic acid (6 mL) was stirred at room temperature for three hours. Saturated potassium carbonate was added until the pH was basic, and the reaction mixture was extracted with methylene chloride (3×). The combined organic extracts were dried and concentrated to yield 2.36 g (75%) of the free amine as a thick oil, $^1$H NMR (300 Mhz, CDCl$_3$): δ1.87–2.20 (m, 6H); 2.79 (m, 2H); 3.03–3.15 (m, 4H total); 3.84 (m, 1H); 7.32 (m, 1H); 7.60 (m, 1H); 8.57 (m, 2H).

3-(3-Pyridyl)-1-propylmercaptyl 2S-1-[(2-methylbutyl)carbamoyl]pyrrolidine-2-carboxylate (1)

A solution of 2-methylbutylamine (113 mg; 1.3 mmol) and triethylamine (132 mg; 1.3 mmol) in methylene chloride (5 mL) was added to a solution of triphosgene (128 mg; 0.43 mmol) in methylene chloride (5 mL). The resulting mixture was refluxed for 1 hour and then cooled to room temperature. 3-(3-Pyridyl)-1-propylmercaptyl pyrrolidine-2-carboxylate (300 mg; 1.3 mmol) in 5 mL of methylene chloride was added and the resulting mixture was stirred for 1 hour and then partitioned between water and a 1:1 mixture of ethyl acetate and hexane. The organic phase was dried, concentrated and purified by column chromatography (50% ethyl acetate/hexane) to obtain 250 mg (55%) of the compound of Example 1 (1, Table I) as an oil, $^1$H NMR (300 MHz, CDCl$_3$): d $^1$H NMR (CDCl$_3$, 300 MHz) : δ0.89–0.93 (m, 6H); 1.10–1.20 (m, 1H); 1.27 (s, 1H); 1.36–1.60 (m, 2H); 1.72 (s, 2H); 1.97–2.28 (m, 6H); 2.70–2.75 (m, 2H); 2.92–3.54 (m, 6H); 4.45–4.47 (m, 1H); 7.21–7.29 (m, 1H); 7.53–7.56 (dd, 1H); 8.46–8.48 (s, 2H).

Example 2

Synthesis of 3-(3-Pyridyl)-1-propyl 2S-1-[(1', 1'-Dimethylpropyl)carbamoyl]pyrrolidine-2-carboxylate (2)

Reaction of 3-(3-pyridyl)-1-propylmercaptyl pyrrolidine-2-carboxylate with the isocyanate generated from tert-amylamine and triphosgene, as described for Example 1, provided the compound of Example 2 (2, Table 1) in 62% yield, $^1$H NMR (CDCl$_3$, 300 MHz): δ0.83 (t, 3H); 1.27 (s, 6H); 1.64–1.71 (m, 2H); 1.91–2.02 (m, 7H); 2.66–2.71 (t, 2H); 2.85 (m, 2H); 3.29–3.42 (m, 2H); 4.11 (br, 1H); 4.37–4.41 (m, 1H).

Example 3

Synthesis of 3-(3-pyridyl)-1-propylmercaptyl 2S-1-[(cyclohexyl)thiocarbamoyl]-pyrrolidine-2-carboxylate (7)

A mixture of cyclohexylisothiocyanate (120 mg; 0.9 mmol), 3-(3-pyridyl)-1-propylmercaptyl pyrrolidine-2-carboxylate (200 mg; 0.9 mmol) and triethylamine (90 mg; 0.9 mmol) in 20 mL of methylene chloride was the resulting mixture was stirred for 1 hour and then partitioned between water and a 1:1 mixture of ethyl acetate and hexane. The organic phase was dried, concentrated and purified by column chromatography (50% ethyl acetate/hexane) to obtain 160 mg (47%) of the compound of Example 3 (7, Table I), $^1$H NMR (CDCl$_3$, 300 MHz): δ1.16–1.40 (m, 6H) 1.50–1.71 (m, 4H); 1.95–2.08 (m, 7H); 2.70–2.75 (t, 2H); 3.03 (m, 2H); 3.40–3.60 (m, 2H); 4.95–4.98 (d, 1H); 5.26–5.29 (d, 1H); 7.17–7.25 (m, 1H).

As discussed, the compounds of the present invention have an affinity for the FK506 binding protein, particularly FKBP12. The inhibition of the prolyl peptidyl cis-trans isomerase activity of FKBP may be measured as an indicator of this affinity.

Ki Test Procedure

Inhibition of the peptidyl-prolyl isomerase (rotamase) activity of the inventive compounds can be evaluated by known methods described in the literature (Harding, et al., Nature, 1989, 341:758–760; Holt et al. J. Am. Chem. Soc., 115:9923–9938). These values are obtained as apparent Ki's and are presented in Table II. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent Ki values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

The data for these experiments for representative compounds are presented in Table II under the column "Ki".

The neurotrophic effects of the compounds of the present invention can be demonstrated in cellular biological experiments in vitro, as described below.

Chick Dorsal Root Ganglion Cultures and Neurite Outgrowth

Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 μM cytosine β-D arabinofuranoside (Ara C) at 37° C. in an environment containing 5% $CO_2$. Twenty-four hours later, the DRGs were treated with various immunophilin ligands. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and eachtreatment was performed in duplicate.

The data for these experiments for representative compounds are presented in Table II under the column "$ED_{50}$".

TABLE II

In Vitro Test Results

| Ex. No. | Ki, nM[a] | ED50, nM[a] |
|---|---|---|
| 1 | +++ | ++++ |
| 2 | ++ | +++ |
| 3 | ++ | +++ |
| 4 | ++ | ++ |
| 5 | ++ | +++ |
| 6 | + | ++ |
| 7 | ++ | +++ |
| 8 | +++ | ++++ |
| 9 | +++ | ++++ |
| 10 | +++ | +++ |
| 11 | ++ | +++ |
| 12 | +++ | +++ |
| 13 | +++ | ++++ |
| 14 | +++ | +++ |
| 15 | +++ | ++++ |
| 16 | ++ | ++ |

[a]Relative potencies of compounds are ranked according to the following scale: ++++ denotes Ki or ED50 < 1 nM; +++ denotes Ki or ED50 of 1–50 nM; ++ denotes Ki or ED 50 of 51–200 nM; + denotes Ki or ED of 201–500 nM.

MPTP Model of Parkinson's Disease

The remarkable neurotrophic and neuroregenerative effects of the present inventive compounds can be further demonstrated in an animal model of neurodegenerative disease. MPTP lesioning of dopaminergic neurons in mice is used as an animal model of Parkinson's Disease. Four week old male CD1 white mice are dosed i.p. with 30 mg/kg of MPTP for 5 days. Test compounds (4 mg/kg), or vehicle, are administered s.c. along with the MPTP for 5 days, as well as for an additional 5 days following cessation of MPTP treatment. At 18 days following MPTP treatment, the animals are sacrificed and the striata are dissected and perfusion-fixed. Immunostaining is performed on saggital and coronal brain sections using anti-tyrosine hydroxylase 1 g to quantitate survival and recovery of dopaminergic neurons. In animals treated with MPTP and vehicle, a substantial loss of functional dopaminergic terminals is observed as compared to non-lesioned animals. Lesioned animals receiving test compounds show a significant recovery of TH-stained dopaminergic neurons. Data from this model presents quantitation for the recovery of TH-positive dopaminergic neurons in the striatum of animals receiving the compounds of the present invention. Data from representative control and lesioned animals not receiving the test drugs also presents quantitation of effects in the absence of the compounds of the present invention.

The invention being thus described, it will be obvious that the same may be varied in many ways. Such variations are not to be regarded as a departure from the spirit and scope of the invention and all such modifications are intended to be included within the scope of the following claims.

What is claimed is:

1. A compound of formula I:

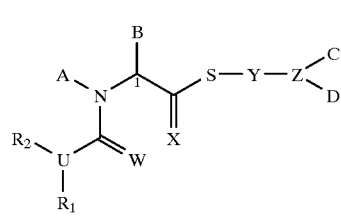

or a pharmaceutically acceptable salt thereof, wherein:

A and B are taken together, with the nitrogen and carbon atoms to which they are respectively attached, to form a pyrrolidine ring;

X is either O or S;

Y is a direct bond to Z, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

Z is a direct bond, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

C and D are independently:

hydrogen, or Ar, or $C_1$–$C_6$ straight or branched chain alkyl or alkenyl which is optionally substituted in one or more position(s) with $C_3$–$C_8$ cycloalkyl, $C_5$–$C_7$ cycloalkenyl, hydroxyl, carbonyl oxygen, or with Ar, where said alkyl, alkenyl, cycloalkyl or cycloalkenyl groups is optionally substituted with $C_1$–$C_4$ alkyl, $C_1$–$C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

wherein Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, or a combination thereof; wherein aromatic or tertiary alkyl amines are optionally oxidized to a corresponding N-oxide;

W is oxygen or sulfur;

U is either O or N, wherein when U is O, then $R_1$ is a lone pair of electrons and $R_2$ is selected from the group consisting of Ar, as defined above, or $C_3$–$C_8$ cycloalkyl, or $C_1$–$C_6$ straight or branched chain alkyl or alkenyl, or $C_1$–$C_6$ straight or branched chain alkyl or alkenyl substituted in one or more positions with Ar as defined above, or with $C_3$–$C_8$ cycloalkyl;

and when O is N, $R_1$ and $R_2$ are selected independently from the group consisting of Hydrogen, or Ar, as defined above, or $C_3$–$C_8$ cycloalkyl, or $C_1$–$C_6$ straight or branched chain alkyl or alkenyl, or $C_1$–$C_6$ straight or branched chain alkyl or alkenyl substituted in one or more positions with Ar as defined above, or with $C_3$–$C_8$ cycloalkyl, or R1 and R2 may be taken together to form a heterocyclic 5 membered ring selected from the following: pyrrolidine.

2. The compound of claim 1, wherein the mono- or bicyclic, carbo- or heterocyclic ring is selected from the group consisting of naphthyl, indolyl, furyl, thiazolyl, thienyl, pyridyl, quinolinyl, isoquinolinyl, fluorenyl and phenyl.

3. The compound of claim 1, wherein the compound has an affinity for FKBP-type immunophilins.

4. The compound of claim 3, wherein the FKBP-type immunophilins are FKBP12.

5. The compound of claim 1, wherein the compound inhibits rotamase enzyme activity.

6. The compound of claim 1, wherein the compound is selected from the group consisting of:

3-(para-Methoxyphenyl)-1-propylmercaptyl(2S)-N-(benzenesulfonyl)pyrrolidine-2-carboxylate(4);

3-(para-Methoxyphenyl)-1-propylmercaptyl(2S)-N-(α-toluenesulfonyl)pyrrolidine-2-carboxylate (5); and 3-(para-Methoxyphenyl)-1-propylmercaptyl(2S)-N-(α-toluenesulfonyl)pyrrolidine-2-carboxylate (6).

7. A pharmaceutical composition comprising a neurotrophically effective amount of the compound of claim 1 and a pharmaceutically acceptable carrier.

8. A method of effecting a neuronal activity in an animal, comprising:

administering to the animal a neurotrophically effective amount of the compound of claim 1.

9. The method of claim 6, wherein the neuronal activity is selected from the group consisting of stimulation of damaged neurons, promotion of neuronal regeneration, prevention of neurodegeneration and treatment of neurological disorder.

10. The method of claim 7, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.

11. The method of claim 8, wherein the neurological disorder relating to neurodegeneration is selected from the group consisting of Alzheimer's Disease, Parkinson's Disease, and amyotrophic lateral sclerosis.

12. A compound of formula IV:

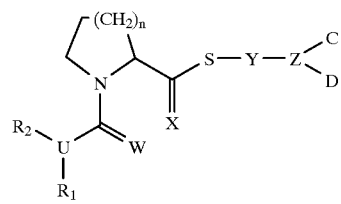

IV or a pharmaceutically acceptable salt thereof, wherein:

n is 1 forming a 5 member heterocyclic ring;

X is either O or S;

Y is a direct bond to Z, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

Z is a direct bond, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

C and D are independently:
hydrogen, or Ar, or $C_1$–$C_6$ straight or branched chain alkyl or alkenyl, which is optionally substituted in one or more position(s) with $C_3$–$C_8$ cycloalkyl, $C_5$–$C_7$ cycloalkenyl, hydroxyl, carbonyl oxygen, or with Ar, where said alkyl, alkenyl, cycloalkyl or cycloalkenyl groups is optionally substituted with $C_1$–$C_4$ alkyl, $C_1$–$C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_3$, S, SO, or $SO_2$, where $R_3$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

wherein Ar is a mono-, bi- or tricyclic, carbo- or heterocyclic ring, wherein the ring is either unsubstituted or substituted in one to three positions(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof; wherein aromatic or tertiary alkyl amines are optionally oxidized to a corresponding N-oxide;

W is oxygen or sulfur;

U is either O or N, wherein when U is O, then $R_1$ is a lone pair of electrons and $R_2$ is selected from the group consisting of Ar, as defined above, or C3–C8 cycloalkyl, or $C_1$–$C_6$ straight or branched chain alkyl or alkenyl, or $C_1$–$C_6$ straight or branched chain alkyl or alkenyl substituted in one or more positions with Ar as defined above, or with C3–C8 cycloalkyl;

and when U is N, $R_1$ and $R_2$ are selected independently from the group consisting of Hydrogen, or Ar, as defined above, or C3–C8 cycloalkyl, or $C_1$–$C_6$ straight or branched chain alkyl or alkenyl, or $C_1$–$C_6$ straight or branched chain alkyl or alkenyl substituted in one or more positions with Ar as defined above, or with C3–C8 cycloalkyl, or R1 and R2 may be taken together to form a heterocyclic 5 membered ring selected from the following: pyrrolidine.

13. The compound of claim 12, wherein Ar is selected from the group consisting of naphthyl, indolyl, furyl, thiazolyl, thienyl, pyridyl, and phenyl.

14. The compound of claim 12, wherein the compound has an affinity for FKBP-type immunophilins.

15. The compound of claim 12, wherein the FKBP-type immunophilins are FKBP12.

16. The compound of claim 12, wherein the compound inhibits rotamase enzyme activity.

17. A pharmaceutical composition comprising a neurotrophically effective amount of the compound of claim 12 and a pharmaceutically acceptable carrier.

18. A method of effecting a neuronal activity in an animal, comprising:

administering to the animal a neurotrophically effective amount of the compound of claim 12.

19. The method of claim 18, wherein the neuronal activity is selected from the group consisting of stimulation of damaged neurons, promotion of neuronal regeneration, prevention of neurodegeneration and treatment of neurological disorder.

20. The method of claim 19, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.

21. The method of claim 20, wherein the neurological disorder relating to neurodegeneration is selected from the group consisting of Alzheimer's Disease, Parkinson's Disease, and amyotrophic lateral sclerosis.

* * * * *

UNITED STATES PATENT AND TRADEMARK OFFICE
CERTIFICATE OF CORRECTION

PATENT NO. : 5,935,989  
DATED : August 10, 1999  
INVENTOR(S) : Gregory S. Hamilton et al.

Page 1 of 1

It is certified that error appears in the above-identified patent and that said Letters Patent is hereby corrected as shown below:

<u>Column 21,</u>
Line 33, after "and when" and before "is N", please replace "O" with -- U --.

Signed and Sealed this

Thirtieth Day of April, 2002

Attest:

Attesting Officer

JAMES E. ROGAN  
*Director of the United States Patent and Trademark Office*

UNITED STATES PATENT AND TRADEMARK OFFICE
CERTIFICATE OF CORRECTION

PATENT NO. : 5,935,989  
DATED : August 10, 1999  
INVENTOR(S) : Gregory S. Hamilton et al.

It is certified that error appears in the above-identified patent and that said Letters Patent is hereby corrected as shown below:

<u>Column 2,</u>  
Line 62, please replace "neurozrophic" with -- neurotrophic --.

Signed and Sealed this

Second Day of July, 2002

Attest:

Attesting Officer

JAMES E. ROGAN  
Director of the United States Patent and Trademark Office